United States Patent [19]

Lagios

[11] Patent Number: 4,462,801
[45] Date of Patent: Jul. 31, 1984

[54] DENTAL ARTICULATORS

[76] Inventor: Peter Lagios, 7S665 Carriage Way, Naperville, Ill. 60540

[21] Appl. No.: 388,020

[22] Filed: Jun. 14, 1982

[51] Int. Cl.³ ............................................. A61C 11/00
[52] U.S. Cl. ...................................................... 433/60
[58] Field of Search ........................................... 433/60

[56] References Cited

U.S. PATENT DOCUMENTS

| | | | |
|---|---|---|---|
| 3,200,497 | 8/1965 | Goodfriend | 433/214 |
| 3,221,408 | 12/1965 | Scullin | 433/60 |
| 3,653,126 | 4/1972 | Hansen | 433/60 |
| 3,808,689 | 5/1974 | Spinella | 433/60 |
| 3,844,040 | 10/1974 | Willis | 433/60 |
| 4,163,319 | 8/1979 | Ouaknine | 433/60 |

FOREIGN PATENT DOCUMENTS 3030585  3/1982  Fed. Rep. of Germany ........ 433/60

Primary Examiner—Robert P. Swiatek
Attorney, Agent, or Firm—Robert V. Jambor

[57] ABSTRACT

There is disclosed an improvement for dental articulators of the Arcon type. The improvement comprises spacer plates adapted to be mounted to the upper and lower frame members of the articulator by the mounting screw of the articulator so that the dental casts with reduced vertical dimension can be mounted between spacers thereby allowing the overall vertical dimension of the dental casts to be reduced to save material and storage space. The improvement also maintains the positional relationship between the frame members and the dental cast by duplicating on the opposing surfaces of the spacers positioning posts in the same position as the positioning posts found on the upper and lower frames. The improvement allows smaller, less costly, more easily stored dental casts to be used without losing any of the capacity of the articulator to duplicate the manipulation of the human mandible.

7 Claims, 4 Drawing Figures

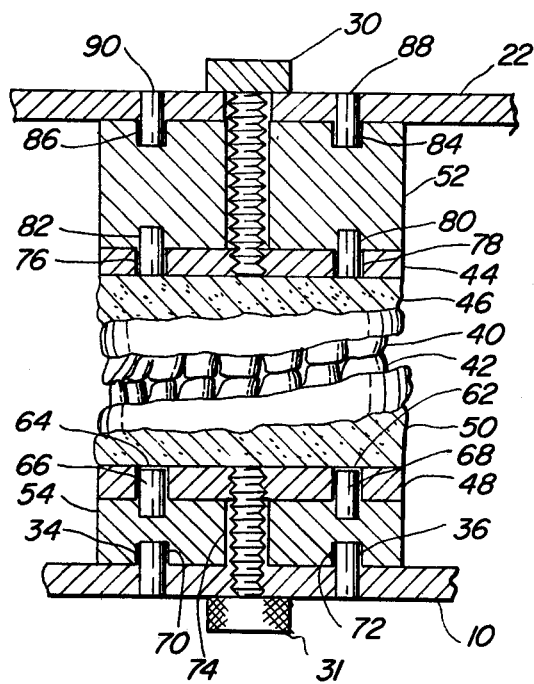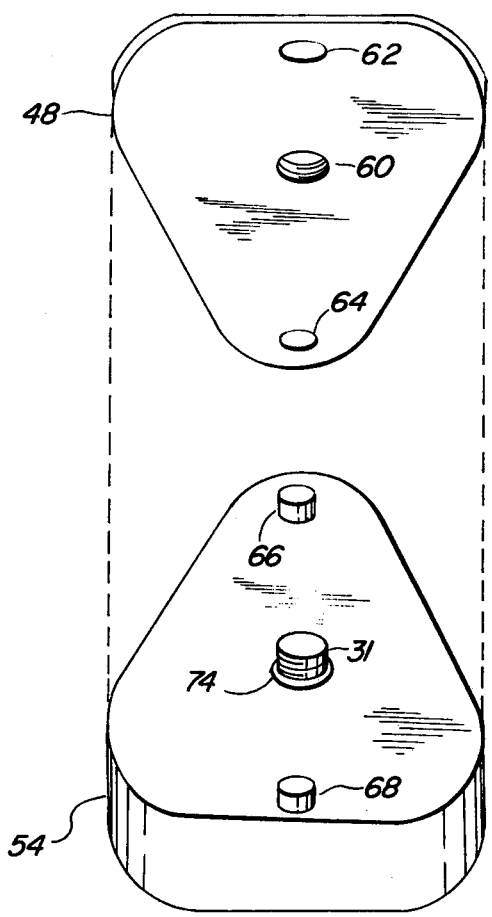

DENTAL ARTICULATORS

BACKGROUND OF THE INVENTION

1. Field of the Invention

The present invention relates to dental equipment and, more particularly, relates to improvements to dental articulators and to methods of use thereof which are employed to simulate mandibular movements.

2. Description of the Prior Art

Dental articulators are well-known in the art and are complex mechanical devices having incisal pin and condylarfossa guides that can be set at many different angles to permit simulation of the mandibular movement so that precise dental measurements and relationships can be determined.

For example, several different types of dental articulators are illustrated in U.S. Pat. Nos. 3,590,487—Guichet, 3,769,708—Guichet and 3,024,640—Guichet.

The principal disadvantage of Arcon type dental articulators of the type illustrated in the foregoing patents is that the distance between the upper and lower frames of the articulator is quite large requiring unduly long and bulky dental casts to be formed to be able to extend between the two frames. Further, since the typical orthodontist has a large number of patients for whom he must keep and store dental cast, the size of the casts has a substantial impact upon the storage space required by the orthodontist. Also, a reduction in the size of the cast will reduce the amount of material necessary to form the casts thereby effectuating a significant savings of material.

Because of the significant increase in the size of the dental casts necessary for the Arcon type dental articulator, many dentists use older out-dated articulators rather than go to the expense of buying new larger storage boxes.

Thus, it would be a desirable advance in the art to provide an improvement to the widely-used Arcon type dental articulator that allows the dental casts used on that type of dental articulator to be substantially reduced in vertical dimension.

BRIEF DESCRIPTION OF THE INVENTION

The present invention is an improvement for a dental articulator of the type having upper and lower frame members, each with means to support dental casts in opposed relationship. The frame members are joined in a manner to permit manipulation of the dental casts to duplicate the movements of the human mandible so that precise dental relationships and measurements may be made.

The improvement comprises a first spacer means for being mounted on the means to support dental casts on the upper frame member. The first spacer means includes means to mount and dismount the upper dental casts in an opposed relationship. The upper dental cast has a reduced vertical dimension that is reduced by an amount equal to the vertical dimension of the first spacer means. The improvement also includes a second spacer means mounted on the means to support dental casts on the lower frame. The second spacer means also includes means to mount and dismount the lower dental cast in an opposed relationship to the upper dental cast. The vertical dimension of the lower dental cast is reduced by the vertical dimension of the second spacer means.

The first and second spacer means include guide means adapted to receive guide pins mounted on the upper and lower frame members so that the first and second spacer means are held in a fixed positional relationship with respect to the frame members.

Further, the first and second spacer means may be provided with openings adapted and positioned to receive mounting screws attached to the upper and lower frame members so that the spacer means may be mounted and dismounted from the upper and lower frame members.

The first and second spacer means also include guide pins extending from the surface opposite the surface contacting the frame members for engaging openings in a mounting plate upon which the dental casts are mounted so that the dental casts are held in a fixed positional relationship when mounted to the spacer means.

The upper first spacer means is of a greater vertical dimension than the lower second spacer means because of the difference in the relationship between the articulator hinge (which duplicates the human jaw hinge) and the point of bite contact between the upper and lower casts as will be more fully explained below.

Thus, it is a principal object of the present invention in reducing the amount of material used for the fabricating and mounting of dental casts on dental articulators thereby reducing the vertical size of the casts and permitting smaller casts that can be stored in conventional storage containers.

Yet another object of the present invention is to permit easier mounting and dismounting of dental casts on articulators while maintaining the correct positional relationship between the frame of the articulator and dental casts.

These and other objectives, advantages and features shall hereinafter appear, and for the purposes of illustration but not for limitation, an exemplary embodiment of the present invention is illustrated in the accompanying drawings.

BRIEF DESCRIPTION OF THE DRAWINGS

FIG. 3 is a cross-sectional view taken substantially along line 3—3 in FIG. 2.

FIG. 4 is a perspective end view of the lower spacer members in accordance with the present invention and mounting plate for the dental casts.

DETAILED DESCRIPTION OF THE PREFERRED EMBODIMENT

Figure 1:
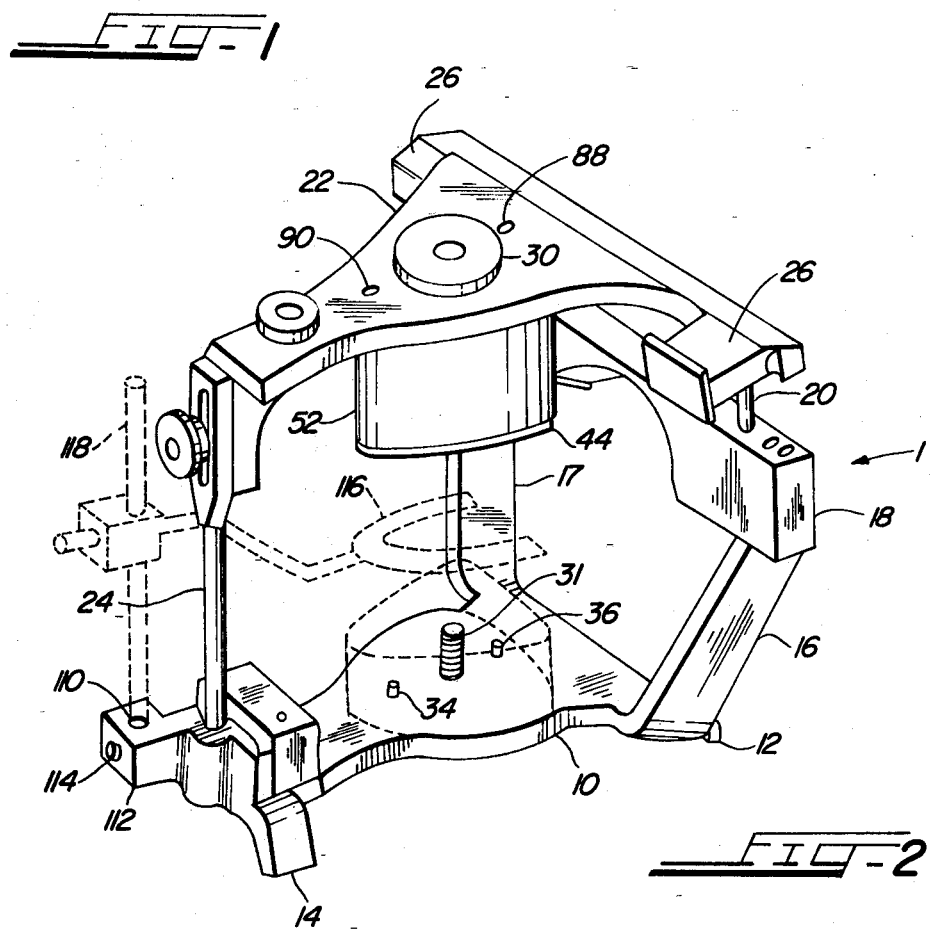
FIG. 1 is an upper right front perspective view of a dental articulator having the upper spacer members mounted thereon in accordance with the present invention and the lower spacer member shown in dotted lines.

With reference to FIG. 1, dental articulator 1 comprises a lower frame 10 supported by rear feet 12 and front feet 14. Frame 10 is essentially triangular in shape with an apex where feet 14 are joined and two upright posts 16 and 17 at opposite sides of the rear portion of frame 10 adjacent feet 12. Mounted between the tops of posts 16 and 17 is a supporting bridge 18. Two upwardly extending shafts 20 are mounted at each end of bridge 18 and condyles (not shown) are mounted on the upper ends of posts 20. The condyles are ball shaped bearing surfaces and support the rear of the upper frame 22. Upper frame 22 is similarly a triangular shaped member with its front anterior end supported by an incisal pin 24. At the opposite end of frame 22 are fossa guide assemblies 26 which rest and pivot on the respective condyles. Thus, the condyles provide hinge connection between the upper and lower frames at their posterior ends.

Dental cast mounting screws 30 and 31 extend through upper frame 22 and lower frame 10, respectively. Pins 34 and 36 extend from the upper surface of lower frame 10 and similar pins 88 and 90 extend downwardly from the bottom surface of frame 22. These pins serve to align and retain the dental casts in a fixed position each time they are mounted.

Figure 2:
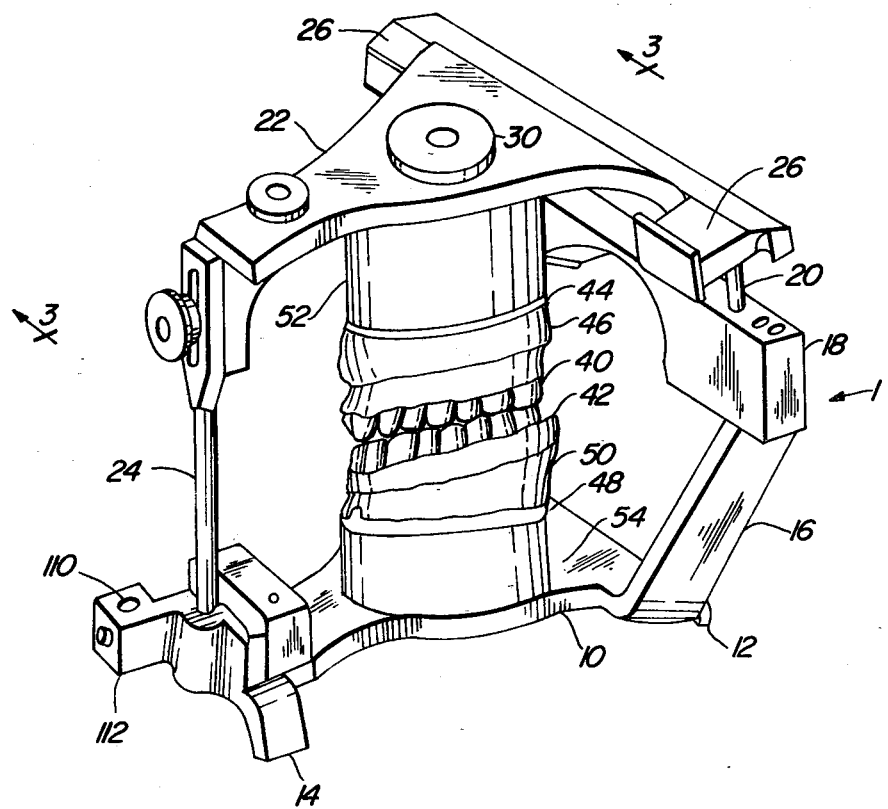
FIG. 2 is an upper right front perspective view of the dental articulator illustrated in FIG. 1 showing dental casts mounted on the spacer members.

With reference to FIG. 2, the upper dental cast 40 and the lower dental cast 42 are shown mounted in an opposed relationship. The upper maxillary cast 40 is mounted to a base plate 44 by plaster of paris or dental stone 46.

Similarly, the lower mandibular cast 42 is mounted to a base plate 48 by plaster of paris or dental stone 50. The base plate 44 is mounted on an upper spacer member 52 and the lower base plate 48 is mounted on a lower spacer member 54. With reference to FIGS. 3 and 4, base plate 48 is identical to base plate 44 and comprises an essentially triangular shaped member having a threaded opening 60 and guide pin openings 62 and 64 positioned to engage guide pins 66 and 68 on spacer member 54. The threaded opening 60 is threaded to mate with mounting screw 31 that extends through spacer 54. On the bottom of spacer 54 are recesses 70 and 72 that are positioned and dimensioned to receive pins 34 and 36. A circular channel 74 is formed through the center of spacer 54 which is slightly larger than the threaded portion of screw 31 to permit screw 31 to freely rotate to engage the threads in base plate 48.

Similarly, upper base plate 44 is mounted to upper spacer member 52 by mounting screw 30. Upper base plate 44 has guide pin openings 76 and 78 which receive guide pins 80 and 82 mounted in the lower surface of spacer 52. Spacer 52 also has recesses 84 and 86 which are dimensioned and positioned to receive pins 88 and 90 mounted in upper frame 22.

Dental casts 40 and 42 are prepared in the conventional manner by taking impressions of the patient's dental structure and then making a cast from the hardened impression. After the dental casts have been prepared, it is necessary to mount the dental casts in the proper position in the articulator so that the instrument will duplicate the anatomic counterpart to simulate the mandibular movement so that precise dental measurements and relationships can be determined.

To mount the dental casts, it is first necessary to determine the precise position between the bite reference plane and the patient's mandibular joint. To accomplish this, a conventional bite fork is covered with base plate wax, inserted between the patient's jaws and aligned with the patient's midline.

With the patient holding the bite fork in place with the jaws, a face bow is mounted with the posterior reference at the external auditory meatus and the anterior reference point at the infra orbital ridge to obtain the patient's horizontal reference plane. A transfer jig is mounted to the face bow and the transfer jig is locked to the bite fork. The transfer jig 118 is then removed from the face bow and mounted on the articular in opening 110 on index table flange 112 and locked with set screw 114 as shown by the dotted lines in FIG. 1. The bite fork 116 will then be positioned between upper and lower frames 10 and 22 in the proper horizontal orientation in relation to the hinge point between the condyles and fossa guides 26.

An upper spacer 52 and a mounting base plate 44 are attached to upper frame 22 by mounting screw 30. The maxillary cast is placed in the bite impression on the bite fork and the space between base plate 44 and the upper edge of the cast is filled with quick-drying dental stone or plaster of paris 46 as illustrated in FIG. 2.

Once the upper cast is set, the incisal pin 24 is adjusted to compensate for the thickness of the bite fork occlusal record. The articulator is inverted and the mandibular cast is placed in the lower bite impression. A spacer 54 and mounting base plate 48 are attached by mounting screw 31 and the space between the mandibular cast 42 and the base plate 48 is filled with quick-drying dental stone or plaster of paris 50.

The spacers 52 and 54 are of different vertical heights because of the relationship of the bite plane of the casts to the upper and lower frame members 10 and 22. Because this bite plane is generally below the mid-point between the upper and lower frame members, and since it is important to provide sufficient space between the two surfaces of the spacer members to allow presentation of the important anatomical points or features of all patients, i.e., vestibule and gingival portions of the jaw, it has been found that the upper spacer member 52 should have a vertical dimension of about 16 to 20 percent of the vertical dimension between the upper and lower frame members 10 and 22. Similarly, the lower spacer member should have a vertical dimension of about 8 to 12 percent of the vertical dimension between the upper and lower frame members 10 and 22.

If the base plates 44 and 48 are mounted directly to upper and lower frame members 22 and 10, a substantial quantity of dental stone or plaster of paris 46 and 50 would have to be used to mount the casts in the proper relationship. This would make the casts substantially larger and more difficult to store and also increase the weight and bulkiness of the casts. By using spacer members 52 and 54, the amount of mounting plaster or stone is substantially reduced and the vertical dimension of the casts is reduced thereby permitting more casts to be stored in an equal space. This savings in space can be very important to the average orthodontist who may have thousands of such casts to store.

Guide pins 34 and 36 assure that the spacer members are always properly positioned on the articulator. Further, the guide pins 76 and 78 on the upper spacer member and pins 66 and 68 on the lower spacer member 54 assure that when the base plates 44 and 48 are mounted on the spacer members 52 and 54, the dental casts 40 and 42 are always properly oriented.

It should be apparent that various alterations, modifications and changes may be made to the present invention without departing from the spirit and scope of the present invention as defined in the appended claims.

I claim:

1. In a dental articulator of the type having upper and lower frame members each with means to support dental casts in opposed relationship, the frame members joined in a manner to permit manipulation of the dental casts to duplicate the movements of the human mandible so that precise dental relationships and measurements may be made, an improvement comprising:

a first spacer means for being mounted on said means to support dental casts on said upper frame member, said first spacer means including means to mount and dismount a maxillary dental cast in the opposed relationship;

a second spacer means for being mounted on said means to support dental casts on the lower frame member, said second spacer means including means to mount and dismount a mandibular dental cast in opposed relationship, said first and second spacer means include guide recesses adapted to receive guide pins mounted on the upper and lower frame members so that said first and second spacer means are held in a fixed positional relationship with respect to said frame members, and said first and second spacer means include guide pins extending from the surface opposite the surface contacting the frame members, said guide pins for engaging openings in a mounting base plate on each of the dental casts so that said dental casts are held in a fixed positional relationship when mounted to said spacer means.

2. An improvement as claimed in claim 1 wherein said first spacer means has a vertical dimension of about 16 to 20 percent of the vertical dimension between the upper and lower frame members, and said second spacer means has a vertical dimension of about 8 to 12 percent of the vertical dimension between the upper and lower frame members.

3. In a dental articulator of the type having upper and lower frame members each with means to support dental casts in opposed relationship, the frame members joined in a manner to permit manipulation of the dental casts to duplicate the movements of the human mandible so that precise dental relationships and measurements may be made, an improvement comprising:

a first spacer means for being mounted on said means to support dental casts on said upper frame member, said first spacer means including means to mount and dismount a maxillary dental cast in the opposed relationship;

a second spacer means for being mounted on said means to support dental casts on the lower frame member, said second spacer means including means to mount and dismount a mandibular dental cast in opposed relationship;

a threaded mounting plate mounted to each of said first and second spacer means adapted and positioned to receive mounting screws attached to the upper and lower frame members;

said first and second spacer means are mounted to said upper and lower frame member by said mounting screws extending through said first and second spacer means and engaging threaded openings in said upper and lower mounting plates which plates are respectively attached to the upper and lower dental casts.

4. In a dental articulator of the type having upper and lower frame members adapted to support dental casts in opposed relationship, the frame members joined in a manner to permit manipulation of the dental casts to duplicate the movement of the human mandible so that precise dental relationships and measurements may be made, an improvement comprising:

a first spacer member mounted to the upper frame member, said spacer member having recesses in one surface that engage positioning pins extending from said upper frame member and said first spacer member has further positioning pins extending from an opposite surface to engage recesses in an upper mounting plate attached to a maxillary dental cast so that the maxillary cast is oriented in a fixed position with respect to said upper frame member;

a second spacer member mounted to the lower frame member, said second spacer member having recesses in one surface that engage positioning pins extending from said lower frame member and said second spacer member has further positioning pins extending from an opposite surface to engage recesses in a lower mounting plate attached to a mandibular dental cast so that the mandibular cast is oriented in a fixed position with respect to said lower frame member.

5. An improvement as claimed in claim 4 wherein said upper and lower mounting plates are held in respective engagement with said upper and lower spacer members by threaded mounting screws extending through said spacer members and engaging a threaded opening in said mounting plates.

6. An improvement as claimed in claim 4 wherein the vertical dimension of said first spacer member is about 16 to 20 percent of the vertical dimension between the upper and lower frame members and the vertical dimension of said second spacer member is about 8 to 12 percent of the vertical dimension between the upper and lower frame members.

7. A method of mounting dental casts on a dental articulator of the type having upper and lower frame members each with means to support dental casts in opposed relationship, the frame members joined in a manner to permit manipulation of the dental casts to duplicate the movements of the human mandible, comprising the steps of:

establishing the bite plane of the patient by having the patient hold a bite fork between the upper and lower jaws;

attaching a face bow to a patient with the posterior reference at the external auditory meatus and the anterior reference at the infra orbital ridge to obtain a horizontal reference plane;

attaching a transfer jig to the face bow;

locking the transfer jig to the bite fork;

removing the transfer jig and bite fork from the face bow and mounting the transfer jig on an articulator index table;

placing the maxillary dental cast in the upper bite impression of the bite fork;

mounting a spacer member and mounting plate on the upper frame member of the articulator;

filling the void between the mounting plate and the maxillary cast with plaster and allowing the plaster to dry;

adjusting the incisal guide pin to accommodate the thickness of the bite fork occlusal record;

inverting the articulator and placing the mandibular cast on the bite fork bite impression;

mounting a spacer member and mounting plate on the lower frame member;

filling the void between the mounting plate and the mandibular cast with plaster and allowing the plaster to dry.

* * * * *